(12) United States Patent
Satoh

(10) Patent No.: US 11,402,198 B2
(45) Date of Patent: Aug. 2, 2022

(54) INFORMATION PROCESSING DEVICE, BIOLOGICAL INFORMATION MEASUREMENT DEVICE, AND COMPUTER-READABLE MEDIUM

(71) Applicant: Naoyuki Satoh, Tokyo (JP)

(72) Inventor: Naoyuki Satoh, Tokyo (JP)

(73) Assignee: RICOH COMPANY, LTD., Tokyo (JP)

(*) Notice: Subject to any disclaimer, the term of this patent is extended or adjusted under 35 U.S.C. 154(b) by 0 days.

(21) Appl. No.: 16/903,778

(22) Filed: Jun. 17, 2020

(65) Prior Publication Data
US 2020/0400429 A1 Dec. 24, 2020

(30) Foreign Application Priority Data

Jun. 19, 2019 (JP) ............................. JP2019-114043
May 22, 2020 (JP) ............................. JP2020-090042

(51) Int. Cl.
*G01B 11/25* (2006.01)
*G06T 7/521* (2017.01)
(Continued)

(52) U.S. Cl.
CPC ............... *G01B 11/25* (2013.01); *A61B 5/055* (2013.01); *A61B 5/369* (2021.01); *G06T 7/521* (2017.01); *G06T 15/87* (2013.01); *G06T 17/20* (2013.01)

(58) Field of Classification Search
CPC ....... A61B 5/0035; A61B 5/055; A61B 5/245; A61B 5/369; A61B 5/4244; A61B 5/7425;
(Continued)

(56) References Cited

U.S. PATENT DOCUMENTS 5,880,737 A * 3/1999 Griffin .................... G06T 15/60
345/582
8,553,961 B2 * 10/2013 Zhu .......................... G06T 7/38
382/131
(Continued)

FOREIGN PATENT DOCUMENTS

JP 2003-044531 2/2003
JP 4896470 1/2012
(Continued)

*Primary Examiner* — Peter D Le
(74) *Attorney, Agent, or Firm* — Harness, Dickey & Pierce, P.L.C.

(57) ABSTRACT

An information processing device includes a displaced position calculation processing unit, a spatial value acquisition processing unit, and a spatial value display processing unit. The displaced position calculation processing unit is configured to determine displaced position data on a position displaced from an optional point on surface shape data on a surface of a measurement target in a given direction by a given distance. The spatial value acquisition processing unit is configured to acquire, based on spatial region values represented by volume data formed in a space containing a shape of the measurement target and the displaced position data, a spatial region value for a position stored in the displaced position data. The spatial value display processing unit is configured to dispose and display a display material corresponding to the spatial region value on the surface shape data.

20 Claims, 15 Drawing Sheets

(51) Int. Cl.
*G06T 17/20* (2006.01)
*A61B 5/055* (2006.01)
*G06T 15/87* (2011.01)
*A61B 5/369* (2021.01)

(58) Field of Classification Search
CPC ....... A61B 6/032; A61B 6/037; A61B 6/4417; A61B 6/501; A61B 6/5235; A61B 6/5247; G01B 11/25; G06T 15/87; G06T 17/20; G06T 19/20; G06T 2210/41; G06T 2219/2012; G06T 7/52
See application file for complete search history.

(56) References Cited

U.S. PATENT DOCUMENTS

| | | | | |
|---|---|---|---|---|
| 8,988,461 | B1* | 3/2015 | Schmid | G06T 19/20 |
| | | | | 345/629 |
| 9,149,183 | B2* | 10/2015 | Iwase | A61B 3/102 |
| 10,186,049 | B1* | 1/2019 | Boardman | G06T 7/75 |
| 10,335,037 | B2* | 7/2019 | Jolly | G06K 9/4671 |
| 10,748,351 | B1* | 8/2020 | Hu | G06T 7/596 |
| 10,776,998 | B1* | 9/2020 | Wang | G01R 33/3607 |
| 11,026,749 | B1* | 6/2021 | Chatzizisis | G06T 17/20 |
| 2001/0040999 | A1* | 11/2001 | Fukuda | G06T 15/87 |
| | | | | 382/162 |
| 2002/0021780 | A1* | 2/2002 | Kohler | A61B 6/4035 |
| | | | | 378/15 |
| 2002/0143249 | A1* | 10/2002 | Tornai | A61B 6/037 |
| | | | | 600/425 |
| 2002/0159074 | A1* | 10/2002 | Kawachi | G01B 11/002 |
| | | | | 356/616 |
| 2003/0052875 | A1* | 3/2003 | Salomie | G06T 17/20 |
| | | | | 345/419 |
| 2003/0063703 | A1* | 4/2003 | Moore | A61B 6/035 |
| | | | | 378/17 |
| 2003/0072406 | A1* | 4/2003 | Yang | A61B 6/027 |
| | | | | 378/4 |
| 2003/0088179 | A1* | 5/2003 | Seeley | A61B 6/4441 |
| | | | | 600/424 |
| 2003/0202637 | A1* | 10/2003 | Yang | G06T 11/006 |
| | | | | 378/210 |
| 2004/0021662 | A1* | 2/2004 | Taubin | G06T 9/00 |
| | | | | 345/419 |
| 2004/0082882 | A1* | 4/2004 | Rines | A61N 7/00 |
| | | | | 601/2 |
| 2004/0097800 | A1* | 5/2004 | Crosetto | G01T 1/2985 |
| | | | | 600/407 |
| 2004/0109529 | A1* | 6/2004 | Eberhard | A61B 6/025 |
| | | | | 378/23 |
| 2004/0254456 | A1* | 12/2004 | Ritter | A61B 6/466 |
| | | | | 600/425 |
| 2006/0120582 | A1* | 6/2006 | Squilla | A61C 9/004 |
| | | | | 382/128 |
| 2007/0183560 | A1* | 8/2007 | Popescu | G01N 23/041 |
| | | | | 378/5 |
| 2007/0242798 | A1* | 10/2007 | Popescu | A61B 6/56 |
| | | | | 378/21 |
| 2007/0268287 | A1* | 11/2007 | Magnin | A61B 8/483 |
| | | | | 345/419 |
| 2008/0030744 | A1* | 2/2008 | Beardsley | G01B 11/2527 |
| | | | | 356/601 |
| 2009/0174710 | A1* | 7/2009 | Sim | G06K 9/00201 |
| | | | | 345/420 |
| 2011/0103666 | A1* | 5/2011 | Ohishi | G06T 19/003 |
| | | | | 382/131 |
| 2011/0123077 | A1 | 5/2011 | Goto | |
| 2011/0274324 | A1 | 11/2011 | Clements et al. | |
| 2012/0195482 | A1* | 8/2012 | Wakai | G01R 33/5608 |
| | | | | 382/128 |
| 2012/0294534 | A1* | 11/2012 | Watanabe | G06F 30/17 |
| | | | | 382/195 |
| 2012/0295527 | A1* | 11/2012 | Hattori | A22C 17/0086 |
| | | | | 452/136 |
| 2013/0051645 | A1* | 2/2013 | Kim | G06K 9/00 |
| | | | | 382/131 |
| 2014/0320815 | A1* | 10/2014 | Steinmueller | A61B 3/107 |
| | | | | 351/206 |
| 2015/0133770 | A1 | 5/2015 | Clements et al. | |
| 2015/0193961 | A1 | 7/2015 | Nakagawa et al. | |
| 2015/0302594 | A1* | 10/2015 | Moore | G01B 11/25 |
| | | | | 348/47 |
| 2016/0000299 | A1* | 1/2016 | Itai | A61B 1/31 |
| | | | | 600/103 |
| 2016/0364912 | A1* | 12/2016 | Cho | G06K 9/00214 |
| 2017/0123077 | A1 | 5/2017 | Goto | |
| 2018/0115757 | A1* | 4/2018 | Chuang | H04N 9/735 |
| 2019/0090749 | A1* | 3/2019 | Leuthardt | G06K 9/6277 |

FOREIGN PATENT DOCUMENTS

| | | |
|---|---|---|
| JP | 4896470 | 3/2012 |
| JP | 2013-530028 | 7/2013 |
| JP | 5392644 | 10/2013 |
| JP | 5392644 | 1/2014 |
| JP | 6026932 | 10/2016 |
| JP | 6026932 | 11/2016 |
| JP | 6215057 | 9/2017 |
| JP | 6215057 | 10/2017 |

* cited by examiner

FIG.6

| VERTEX ID | X | Y | Z |
|---|---|---|---|
| 1 | | | |
| 2 | | | |
| ... | | | |
| N | | | |

| TRIANGLE ID | VERTEX ID | VERTEX ID | VERTEX ID |
|---|---|---|---|
| 1 | | | |
| 2 | | | |
| ... | | | |
| M | | | |

| VERTEX ID | X | Y | Z |
|---|---|---|---|
| 1 | | | |
| 2 | | | |
| ... | | | |
| N | | | |

FIG.10

| VERTEX ID | VALUE |
|---|---|
| 1 | |
| 2 | |
| ... | |
| N | |

FIG.11

| VALUE | R | G | B |
|---|---|---|---|
| -4.0 | | | |
| -2.0 | | | |
| 0.0 | | | |
| 2.0 | | | |
| 4.0 | | | |

FIG.16

| SURFACE ID | u | v | X | Y | Z |
|---|---|---|---|---|---|
| 1 | | | | | |
| 2 | | | | | |
| ... | | | | | |
| N | | | | | |

FIG.17

| SURFACE ID | u | v | VALUE |
|---|---|---|---|
| 1 | | | |
| 2 | | | |
| ... | | | |
| N | | | |

INFORMATION PROCESSING DEVICE, BIOLOGICAL INFORMATION MEASUREMENT DEVICE, AND COMPUTER-READABLE MEDIUM

CROSS-REFERENCE TO RELATED APPLICATIONS

The present application claims priority under 35 U.S.C. § 119 to Japanese Patent Application No. 2019-114043, filed on Jun. 19, 2019, and Japanese Patent Application No. 2020-90042, filed on May 22, 2020. The contents of which are incorporated herein by reference in their entirety.

BACKGROUND OF THE INVENTION

1. Field of the Invention

The present invention relates to an information processing device, a biological information measurement device, and a computer-readable medium.

2. Description of the Related Art

Conventionally, it has been known to project values inside a measurement target on the surface of the measurement target. For example, Japanese Patent No. 6026932 discloses a technique in which a projection image in a particular region to be visualized present inside an organ of a subject as a measurement target is projected and displayed on a three-dimensional image of the organ of the subject.

US 2019/0236824 discloses a technique for displaying information such that the information is superimposed on a tomographic image (MR image) of the head of a subject.

However, the technique disclosed in Japanese Patent No. 6026932 has a problem in that, if a viewpoint position for an organ of a subject as a measurement target changes, a value superimposed on the surface of a three-dimensional image of the organ of the subject also changes, and a region sectioned on the surface of the three-dimensional image of the organ of the subject cannot be absolutely associated with the inside of the organ of the subject.

The technique disclosed in US 2019/0236824 has a problem in that signal values inside the brain of a subject cannot be projected on the surface of the brain and hence the values inside the brain cannot be observed in association with a region sectioned on the surface of the brain.

SUMMARY OF THE INVENTION

According to an aspect of the present invention, an information processing device includes a displaced position calculation processing unit, a spatial value acquisition processing unit, and a spatial value display processing unit. The displaced position calculation processing unit is configured to determine displaced position data on a position displaced from an optional point on surface shape data on a surface of a measurement target in a given direction by a given distance. The spatial value acquisition processing unit is configured to acquire, based on spatial region values represented by volume data formed in a space containing a shape of the measurement target and the displaced position data, a spatial region value for a position stored in the displaced position data. The spatial value display processing unit is configured to dispose and display a display material corresponding to the spatial region value on the surface shape data.

BRIEF DESCRIPTION OF THE DRAWINGS

FIG. 6 is a diagram exemplarily illustrating a polygon mesh;

FIG. 10 is a diagram exemplarily illustrating spatial value data;

FIG. 11 is a diagram exemplarily illustrating a color map;

FIG. 16 is a diagram exemplarily illustrating offset position data; and

FIG. 17 is a diagram exemplarily illustrating spatial value data.

The accompanying drawings are intended to depict exemplary embodiments of the present invention and should not be interpreted to limit the scope thereof. Identical or similar reference numerals designate identical or similar components throughout the various drawings.

DESCRIPTION OF THE EMBODIMENTS

Figure 1:
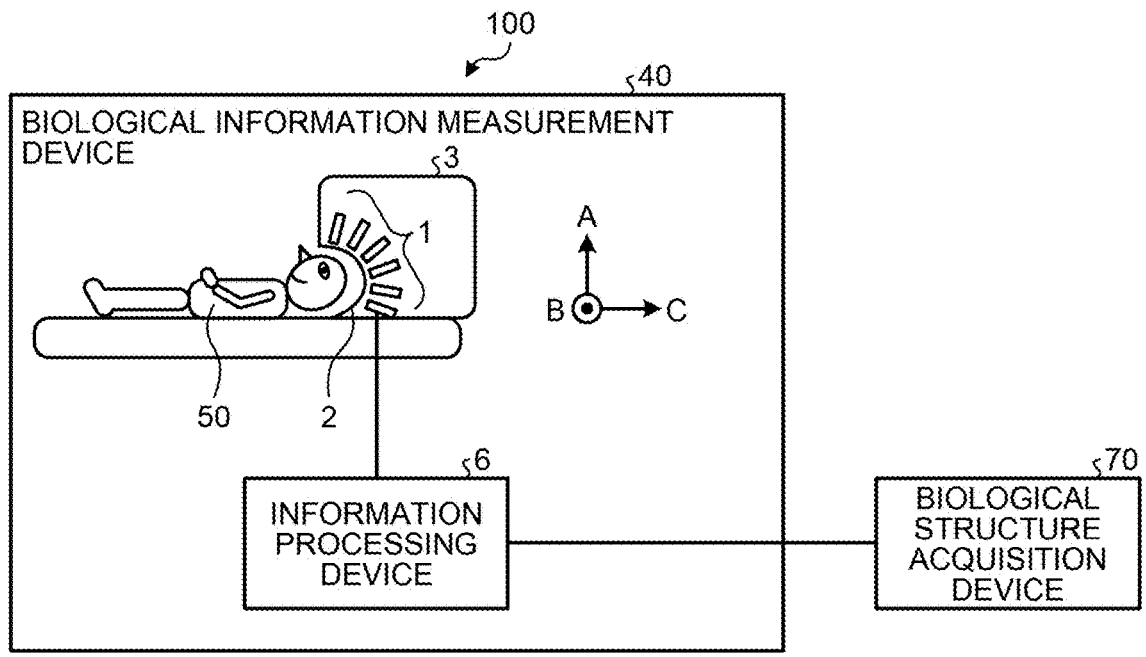
FIG. 1 is a diagram illustrating an example of a system configuration of a biological information measurement system according to a first embodiment.

The terminology used herein is for the purpose of describing particular embodiments only and is not intended to be limiting of the present invention.

As used herein, the singular forms "a", "an" and "the" are intended to include the plural forms as well, unless the context clearly indicates otherwise.

In describing preferred embodiments illustrated in the drawings, specific terminology may be employed for the sake of clarity. However, the disclosure of this patent specification is not intended to be limited to the specific terminology so selected, and it is to be understood that each specific element includes all technical equivalents that have the same function, operate in a similar manner, and achieve a similar result.

An embodiment of the present invention will be described in detail below with reference to the drawings.

An embodiment has an object to enable spatial region values located inside a measurement target to be observed on the surface of the measurement target.

Referring to the accompanying drawings, embodiments of an information processing device, a biological information measurement device, a method for displaying spatial region values, and a computer program are described in detail below.

First Embodiment

FIG. 1 is a diagram illustrating an example of a system configuration of a biological information measurement system 100 according to a first embodiment. As illustrated in FIG. 1, the biological information measurement system 100 includes a biological information measurement device 40 and a biological structure acquisition device 70. For example, the biological structure acquisition device 70 is an MR image device configured to take magnetic resonance (MR) images. The biological structure acquisition device 70 is not limited to an MR image device, and may be an X-ray computed tomography (CT) image device.

The biological information measurement device 40 includes a brain magnetic field measurement device 3 and an information processing device 6.

The brain magnetic field measurement device 3 is a device configured to measure a magneto-encephalography (MEG) signal of a brain that is an organ of a subject as a measurement target. For measurement of the biomagnetic field (brain magnetic field) as biological information on a subject 50 to be measured, the head of the subject 50 is fitted to a dewar 2 of the brain magnetic field measurement device 3 with the head attached with electrodes (or sensors) for brainwave measurement. When the brain waves are not measured at the same time, it is unnecessary to attach the electrodes for brainwave measurement to the head. The dewar 2 is a helmet-type sensor housing dewar that is a cover member surrounding substantially the entire region of the head of the subject 50. A large number of magnetic sensors 1 for brain magnetic measurement are disposed on the inner side of the dewar 2. When a superconducting sensor that requires extremely low temperature environments for its operation (for example, superconducting quantum interference device (SQUID) sensor) is used as the magnetic sensor 1, the dewar 2 also functions as a container for maintaining extremely low temperature environments using liquid helium. The brain magnetic field measurement device 3 collects brainwave signals from the electrodes and magnetoencephalographic signals from the magnetic sensors 1. The brain magnetic field measurement device 3 outputs the collected biological signals to the information processing device 6.

It is noted that, in general, the dewar 2 having the magnetic sensors 1 built therein is disposed in a magnetic shield room, but the magnetic shield room is omitted for the convenience of illustration.

As the magnetic sensors 1, magnetic sensors capable of measuring biomagnetism with magnitude smaller than geomagnetism, such as a SQUID sensor, a tunnel magneto resistance (TMR) sensor, an optically pumped atomic magnetometer (OPM) sensor, or a nitrogen-vacancy (NV) center sensor, can be used. The brain magnetic field measurement device 3 is provided with a plurality of the magnetic sensors 1 such that a generation source of the biomagnetic field (brain magnetic field) can be specified. The relative positions of the magnetic sensors 1 may be permanently fixed or may be arranged as appropriate for each measurement. The relative positions of the magnetic sensors 1 are set to have a certain arrangement at least in a measurement period. A sensor coordinate system is defined for the certain arrangement of the magnetic sensors 1.

It is noted that, in the biological information measurement system 100, signals emitted from neural activity of the brain of the subject 50 are detected by the magnetic sensors 1, but it is not limited thereto. The biological information measurement system 100 only needs to have sensors configured to detect signals emitted from neural activity of the brain, and the sensors are preferably minimally invasive, more preferably non-invasive, in order to accurately measure the biological functions of the subject 50. Examples of such sensors other than magnetic sensors include a brainwave measurement sensor (potential sensor) and an optical topography (near-infrared sensor).

The magnetic sensor 1 in the first embodiment may include a plurality of types of the sensors (such as magnetic sensor, brainwave measurement sensor (potential sensor), and optical topography (near-infrared sensor)). In such a case, however, it is desired that operation of one sensor have no influence on measurement by another sensor. In particular, when a magnetic sensor is used as one of sensors, the mounting state of the sensor has no influence on measurement results because there is a characteristic that signals emitted from a living body can be acquired even when the living body is not in contact with the magnetic sensor. Thus, the magnetic sensor 1 is preferred as an example of the present invention.

The information processing device 6 displays the waveform of magnetoencephalographic signals from the magnetic sensors 1 and the waveform of brainwave signals from a plurality of the electrodes in synchronization with each other on the same time axis. The brainwave signal indicates electric activity of nerve cells (flow of ion charges caused at dendrites of neurons during synaptic transmission) as a potential difference between the electrodes. The magnetoencephalographic signal indicates a minute magnetic field generated by electric activity of the brain and its fluctuation.

A tomographic image (MR image) of the head of the subject 50 taken by the biological structure acquisition device 70 is input in the information processing device 6. The photographing by the biological structure acquisition device 70 may be performed before or after the magnetic measurement by the brain magnetic field measurement device 3. Obtained image data is sent to the information processing device 6 online or offline. The use of a morphological image of the inside of a living body enables detailed analysis of the biomagnetic field.

The information processing device 6 further projects spatial region values indicating activity conditions in the brain measured by the brain magnetic field measurement device 3 to a curved surface indicating the surface of a brain shape imaged by the biological structure acquisition device 70, so that what activity has occurred in the brain in each region sectioned on the brain surface can be intuitively and easily observed. Although the details are described later, the information processing device 6 displays, on the curved surface indicating the surface of the brain, spatial region values at positions obtained by offsetting points on the curved surface indicating the surface of the shape of the brain to the inside of the brain. Here, the regions sectioned on the organ surface are partial regions of an organ sectioned anatomically, such as a Brodmann's brain map for the brain and the Healey and Schroy classification or the Couinaud classification for the liver. It is noted that the spatial region value is not limited to data indicating activity conditions in the brain measured by the brain magnetic field measurement device 3, and a tomographic image (MR image) itself of the head of the subject 50 taken by the biological structure acquisition device 70 can be used.

It is noted that the surface on which spatial region values are projected is not limited to the surface of the brain shape, and may be a mean curved surface obtained by averaging curved surfaces of the brain shape, a circumscribed surface externally touching a curved surface of the brain shape, and an inscribed surface internally touching a curved surface of the brain shape.

Figure 2:
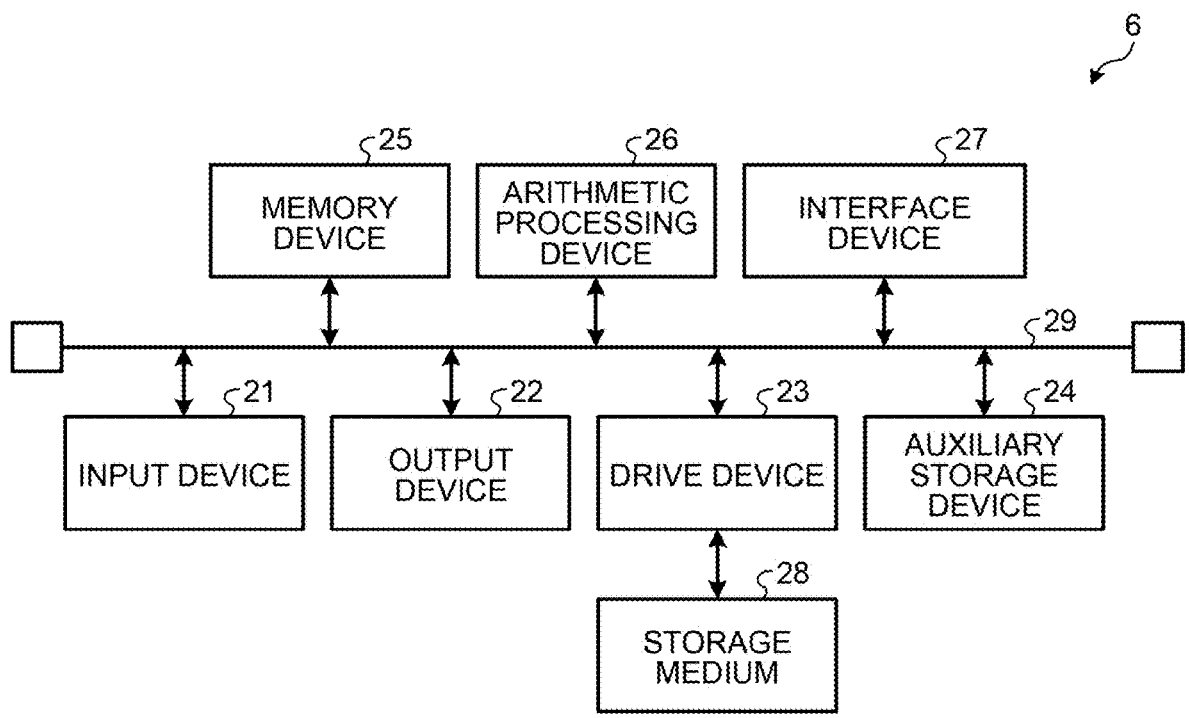
FIG. 2 is a diagram illustrating an example of a hardware configuration of an information processing device.

The information processing device 6 is further described below. FIG. 2 is a diagram illustrating an example of a hardware configuration of the information processing device 6.

The information processing device 6 includes an input device 21, an output device 22, a drive device 23, an auxiliary storage device 24 configured to store a curved surface extraction program and a biological information measurement program therein, a memory device 25, an arithmetic processing device 26, and an interface device 27, which are mutually connected by a bus 29.

The input device 21 is a device configured to input various kinds of information, and is implemented by, for example, a keyboard or a pointing device. The output device 22 is a device configured to output various kinds of information, and is implemented by, for example, a display. The interface device 27 includes a LAN card, and is used for connection to a network.

The curved surface extraction program and the biological information measurement program are at least a part of various computer programs configured to control the information processing device 6. For example, the curved surface extraction program and the biological information measurement program are provided by distribution of a storage medium 28 or by being downloaded from a network. As the storage medium 28 having the curved surface extraction program and the biological information measurement program recorded thereon, various types of storage media such as storage media that optically, electrically, or magnetically record information such as a CD-ROM, a flexible disk, and a magneto-optical disc and semiconductor memories that electrically record information such as a ROM and a flash memory can be used.

When the storage medium 28 having the curved surface extraction program and the biological information measurement program recorded thereon is set to the drive device 23, the curved surface extraction program and the biological information measurement program are installed on the auxiliary storage device 24 from the storage medium 28 through the drive device 23. The biological information measurement program downloaded from a network is installed on the auxiliary storage device 24 through the interface device 27.

The auxiliary storage device 24 stores the installed curved surface extraction program and the installed biological information measurement program therein, and stores necessary files and data therein. When the information processing device 6 is started, the memory device 25 reads the curved surface extraction program and the biological information measurement program from the auxiliary storage device 24, and stores the read computer programs therein. The arithmetic processing device 26 implements various kinds of processing described later in accordance with the curved surface extraction program and the biological information measurement program stored in the memory device 25.

It is noted that the biological structure acquisition device 70 outputs volume data (organ section image group) obtained by laminating sectional images of an organ taken by the biological structure acquisition device 70 such as an MR image device and an X-ray CT image device at a given interval to the information processing device 6. The information processing device 6 stores the volume data (organ section image group) obtained from the biological structure acquisition device 70 in the auxiliary storage device 24.

The information processing device 6 in the first embodiment displays, on a curved surface indicating the surface of the brain, spatial region values from the brain magnetic field measurement device 3 at positions obtained by offsetting points on the curved surface indicating the surface of the shape of the brain to the inside of the brain.

Figure 3:
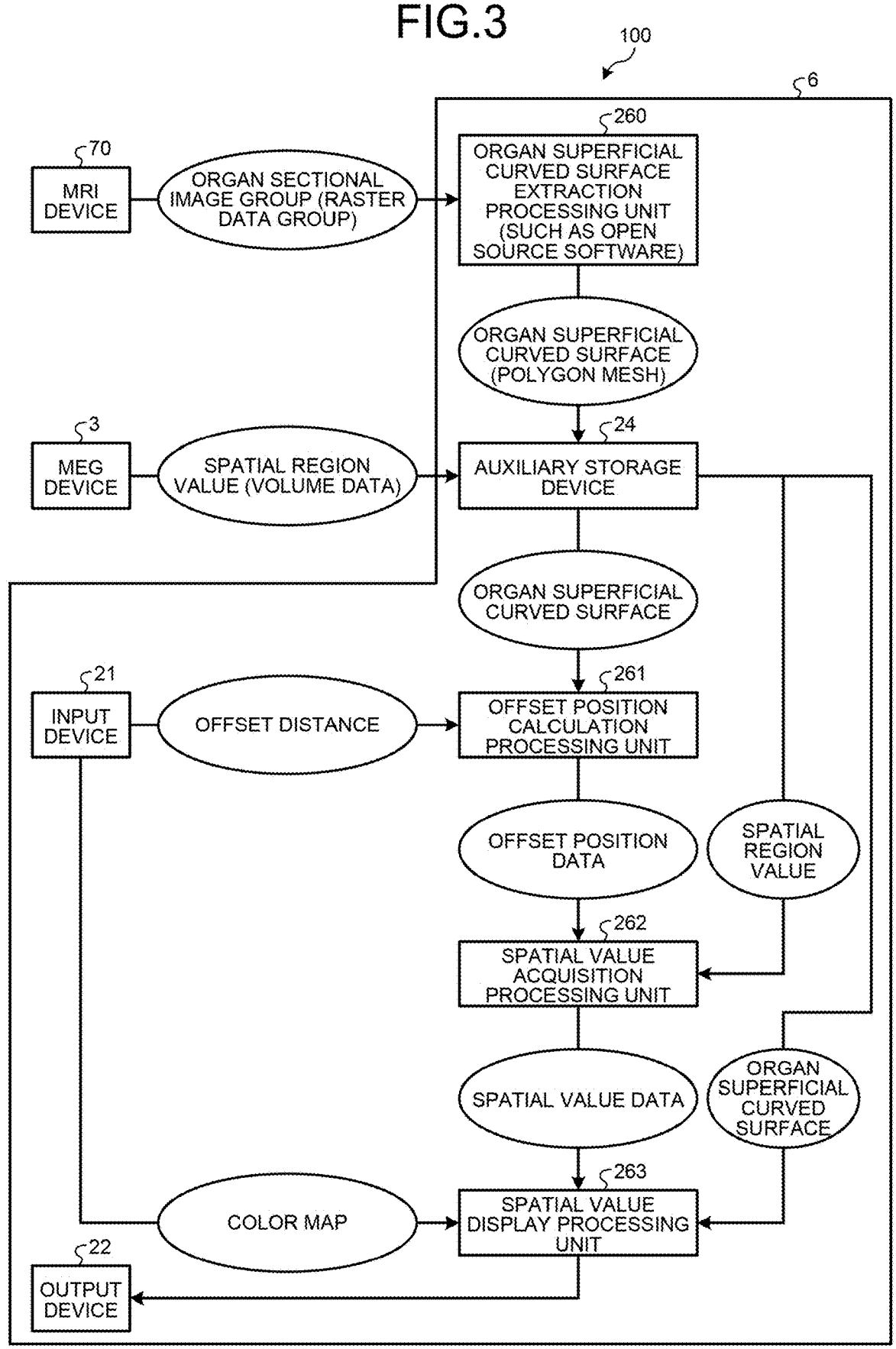
FIG. 3 is a block diagram for describing functions of the information processing device.

Next, characteristic functions among the functions of the information processing device 6 in the first embodiment are described. FIG. 3 is a block diagram for describing the functions of the information processing device 6.

The information processing device 6 has an organ superficial curved surface extraction processing unit 260. The organ superficial curved surface extraction processing unit 260 extracts a curved surface (polygon mesh) as surface shape data on an organ surface (brain surface) from volume data (organ section image group), and stores the curved surface in the auxiliary storage device 24. The arithmetic processing device 26 reads and executes the curved surface extraction program stored in the auxiliary storage device 24 or the memory device 25 to implement the organ superficial curved surface extraction processing unit 260. As the curved surface extraction program, for example, well-known open source software (OSS) can be used.

The information processing device 6 has an offset position calculation processing unit 261 as a displaced position calculation processing unit, a spatial value acquisition processing unit 262, and a spatial value display processing unit 263.

The arithmetic processing device 26 reads and executes the biological information measurement program stored in the auxiliary storage device 24 or the memory device 25 to implement the offset position calculation processing unit 261, the spatial value acquisition processing unit 262, and the spatial value display processing unit 263. The processing units 261 to 263 are described in detail below.

First, the offset position calculation processing unit 261 is described. The offset position calculation processing unit 261 generally generates one or more sample points on a curved surface indicating the surface of an organ shape, and determines the positions of points obtained by moving the sample points in an opposite direction of a unit normal vector of the curved surface at the positions of the sample points (direction from sample points on surface of organ toward inside of organ) by a designated optional distance (offset distance movement).

The offset position calculation processing unit 261 first receives a curved surface (polygon mesh) as surface shape data indicating the surface of the organ shape stored in advance from the auxiliary storage device 24, and receives an offset distance designated by a user from the input device 21. It is noted that the offset distance may be stored in the auxiliary storage device 24 in advance and acquired from the auxiliary storage device 24 without using the input device 21.

Here, the organ shape is data extracted from volume data (organ section image group) obtained by laminating sectional images of the organ taken by the biological structure acquisition device 70 such as an MR image device and an X-ray CT image device at a given interval. The sectional image of the organ is raster data obtained by forming grids in a rectangular planar imaging region at a given interval and allocating values to grid points so as to set values in the rectangular regions.

Figure 4:
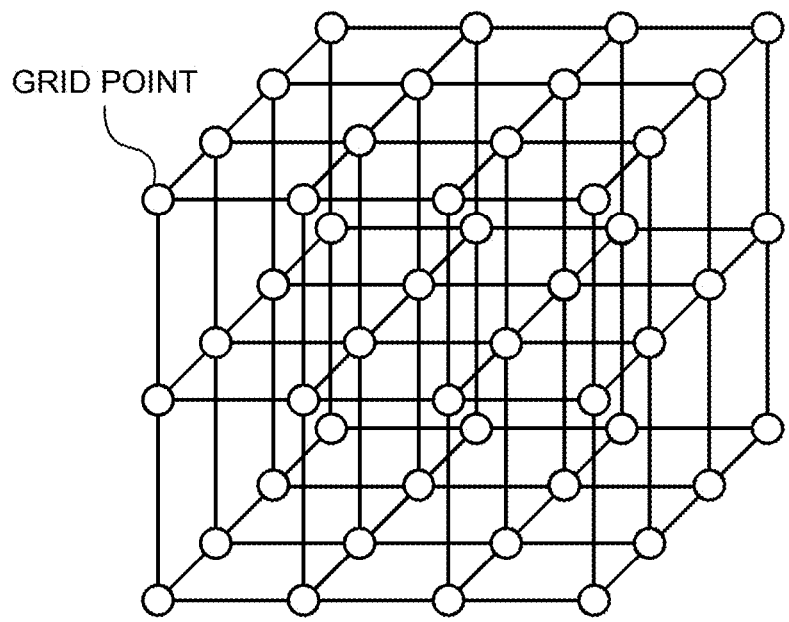
FIG. 4 is a diagram exemplarily illustrating volume data.

FIG. 4 is a diagram exemplarily illustrating volume data. The volume data as illustrated in FIG. 4 is obtained such that sectional images of the organ are laminated at a given interval and thus grids are formed in a rectangular parallelepiped space at a given interval. The value at each grid point in FIG. 4 means the luminance of the image. A gray scale bitmap image is obtained for raster data, and a gray scale volume rendering image is obtained for volume data. The organ shape is extracted by analyzing the luminance of the grid points and grouping a plurality of the grid points. It is noted that the spatial region values are not limited to the ones formed in a rectangular parallelepiped space.

Figure 5:
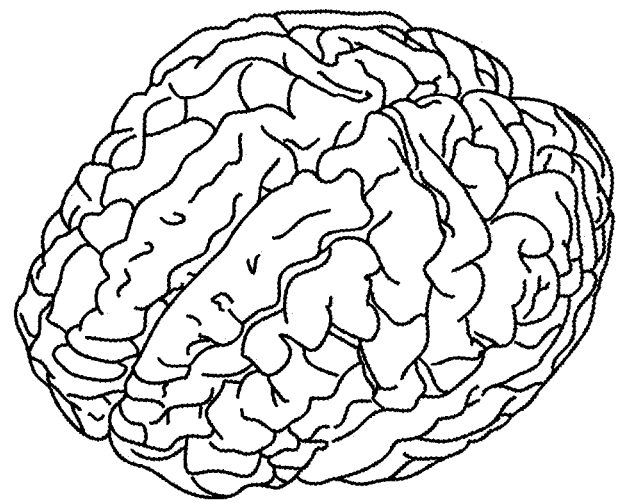
FIG. 5 is a diagram exemplarily illustrating the surface of an organ shape.

FIG. 5 is a diagram exemplarily illustrating the surface of an organ shape. FIG. 5 exemplarily illustrates the brain as an organ. A curved surface indicating the surface of an organ shape as surface shape data is surface data such as a polygon mesh and a polynomial surface or point cloud data obtained by analyzing the organ shape and extracting the contour of the organ, or data obtained by spherical approximation of the polygon mesh, the polynomial surface, or the point cloud data.

FIG. 6 is a diagram exemplarily illustrating a polygon mesh. As illustrated in FIG. 6, the polygon mesh consists of a vertex ID list and a triangle ID list. Positional coordinates of vertices can be acquired from the vertex ID list, and the shape of a polygon and connection information between polygons can be acquired from the triangle ID list.

Figure 7A:
FIGS. 7A and 7B are diagrams exemplarily illustrating a unit normal vector of a curved surface.
Figure 7B:
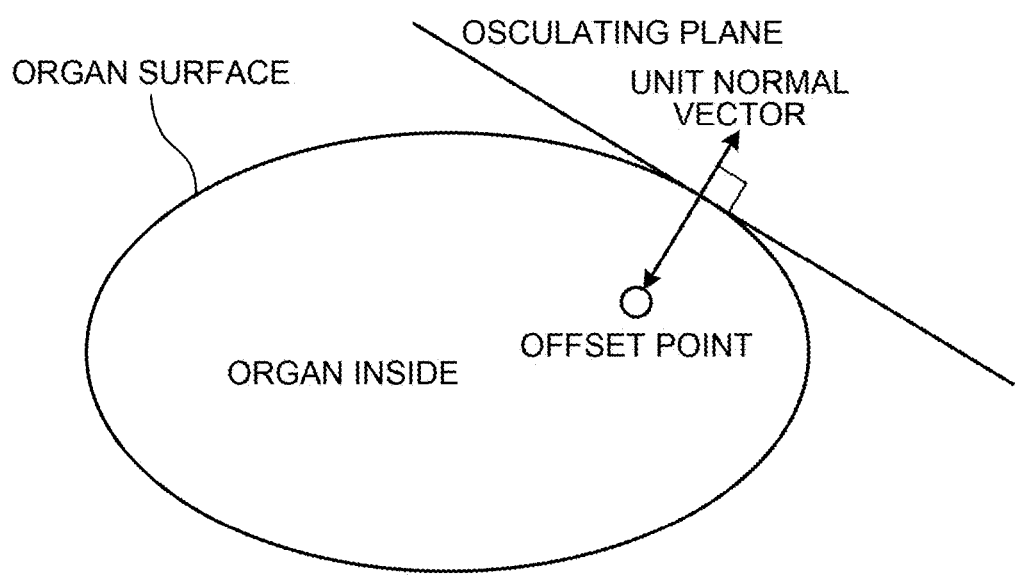

FIGS. 7A and 7B are diagrams exemplarily illustrating a unit normal vector of a curved surface. FIG. 7A is a diagram illustrating an organ section, and FIG. 7B is a diagram exemplarily illustrating a unit normal vector of a curved surface by abstracting the organ section in FIG. 7A.

As illustrated in FIGS. 7A and 7B, next, the offset position calculation processing unit 261 generates one or more sample points on a curved surface (polygon mesh) indicating the surface of the organ shape as surface shape data, and determines the positions of points obtained by moving the sample points in an opposite direction of a unit normal vector of the curved surface at the positions of the sample points by a designated optional distance (offset distance movement).

The position on the curved surface to generate a sample point is optional, but for example, when the curved surface indicating the organ surface is a polygon mesh, vertices forming the polygon mesh can be set as sample points.

The unit normal vector of the curved surface is a unit vector at a point on the curved surface in a direction perpendicular to a plane contacting the point (see FIGS. 7A and 7B). Specifically, a unit normal vector N(u,v) of a polynomial surface S(u,v) is calculated by Equation (1).

$$N(u, v) = \frac{\frac{\partial S}{\partial u} \times \frac{\partial S}{\partial v}}{\left|\frac{\partial S}{\partial u} \times \frac{\partial S}{\partial v}\right|} \quad (1)$$

It is noted that in a case of a polygon mesh, a unit normal vector cannot be calculated at a vertex because an osculating plane cannot be uniquely defined. However, there are some methods for defining a pseudo-unit normal vector from geometric states of polygons around the vertex, and hence a vector determined by such methods is used as a unit normal vector. For example, in an average method, a cross-product vector of two edges connecting to a vertex is determined for each polygon around the vertex (polygon having a corner corresponds to the vertex), and the cross-product vectors of the polygons are averaged to define a pseudo-unit normal vector.

Also in the case of a point cloud, a unit normal vector cannot be calculated because an osculating plane cannot be uniquely defined. However, there are some methods for defining a pseudo-unit normal vector from positions in a point group around a point, and hence a vector determined by such methods are used as a unit normal vector.

In the case where a polynomial surface, a polygon mesh, a point cloud, or a curved surface represented in another form is approximated by a spherical surface, a unit vector in a direction from the spherical center toward a sample point is used as a unit normal vector.

Figures 8, 9:
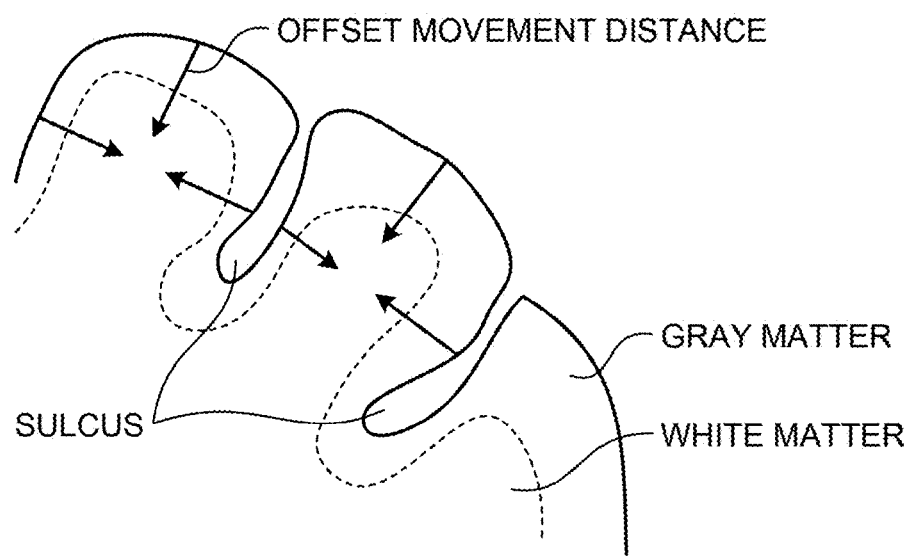
FIG. 8 is a diagram for describing offset distance movement in grooves.
FIG. 9 is a diagram exemplarily illustrating offset position data.

A thin layer (cerebral cortex) of gray matter in the surface of the brain has wrinkles (sulci). FIG. 8 is a diagram for describing offset distance movement in sulci. As illustrated in FIG. 8, in sulci, when a position is moved in an opposite direction of a unit normal vector by a designated optional distance (offset distance movement), it is supposed that the position may go through a convex gyrus formed by sulci. In view of this, in the case where the brain is applied as an organ, if a position goes through a gyrus (moreover, if the position enters self-interference region), a position immediately before entering the self-interference region may be set as an offset position.

The offset position calculation processing unit 261 transfers the determined offset position to the spatial value acquisition processing unit 262 as offset position data (displaced position data).

FIG. 9 is a diagram exemplarily illustrating offset position data. As illustrated in FIG. 9, the offset position data is a list consisting of a set of a vertex ID and positional coordinates. The vertex ID means a vertex ID of a polygon mesh. The positional coordinates mean positional coordinates obtained by offsetting a corresponding vertex.

Next, the spatial value acquisition processing unit 262 is described. The spatial value acquisition processing unit 262 generally determines a spatial region value at the position of a point after offset movement.

The spatial value acquisition processing unit 262 first receives spatial region values represented by volume data stored in advance from the auxiliary storage device 24, and receives offset position data from the offset position calculation processing unit 261.

The spatial region values are data in which values are allocated to coordinate positions in a three-dimensional space. Specifically, the spatial region values are volume data obtained by forming grids at a given interval in a rectangular parallelepiped space containing an organ superficial curved surface as surface shape data and allocating values to grid points so as to set values (real scalar values) in the rectangular parallelepiped region (see FIG. 4). Values at positions other than the grid points are calculated by interpolation with values of surrounding grid points. For the interpolation calculation, there are a plurality of methods such as nearest neighbor interpolation and linear interpolation, and any of the methods may be used. For example, in nearest neighbor interpolation, a value of a grid point at the closest distance is used as a value of that location.

Next, the spatial value acquisition processing unit 262 acquires values from spatial region values for all positions stored in the offset position data. It is noted that "all positions" may be positions obtained by sampling all vertices of a polygon mesh or may be partial several points thereof.

The spatial value acquisition processing unit 262 transfers all the determined values to the spatial value display processing unit 263 as spatial value data.

FIG. 10 is a diagram exemplarily illustrating spatial value data. As illustrated in FIG. 10, the spatial value data is a list including sets each including a vertex ID and a scalar value. The vertex ID means a vertex ID of a polygon mesh. The scalar value means a value acquired from the spatial region value at a position obtained by offsetting a corresponding vertex.

Next, the spatial value display processing unit 263 is described. The spatial value display processing unit 263 generally displays the determined spatial region values at the positions of sample points of a movement source.

The spatial value display processing unit 263 first receives an organ superficial curved surface represented by a polygon mesh stored in advance from the auxiliary storage device 24, receives spatial value data from the spatial value acquisition processing unit 262, and receives a color map designated by a user from the input device 21.

FIG. 11 is a diagram exemplarily illustrating a color map. As illustrated in FIG. 11, the color map is a list including sets each including a value and RGB color elements and arranged according to the value. The value means a value acquired from spatial region values. The RGB color elements mean a color corresponding to the value.

It is noted that a color of a value absent in the list is calculated by linear interpolation with colors of values before and after the value in the list. A color of a value smaller than the minimum value of the values in the list is set to the color of the minimum value in the list, and a color of a value larger than the maximum value of the values in the list is set to the color of the maximum value in the list.

Next, the spatial value display processing unit 263 determines colors corresponding to values stored in the spatial value data from the color map, and sets the colors to all vertices of a polygon mesh.

As a method for displaying a spatial region value by allocating a display material to the position of a sample point of a movement source, some methods are conceivable, such as a method for representing a display material corresponding to the spatial region value by a color as described above and a method for representing a display material corresponding to the spatial region value by a figure (for example, circle). Any method may be used as long as the difference in spatial region value can be recognized by the representation. Such as a method in which, for a position on a curved surface other than a sample point, a value obtained by interpolation with values displayed at surrounding sample point positions is displayed to make it easier to grasp a change in value on the curved surface like a heat map is conceivable. Examples of the interpolation method include Gouraud shading.

The spatial value display processing unit 263 generates an image rendered by set colors, and transfers the image to the output device 22. At this time, interpolation processing based on Gouraud shading is performed for rendering for colors of polygons other than vertices.

Figure 12:
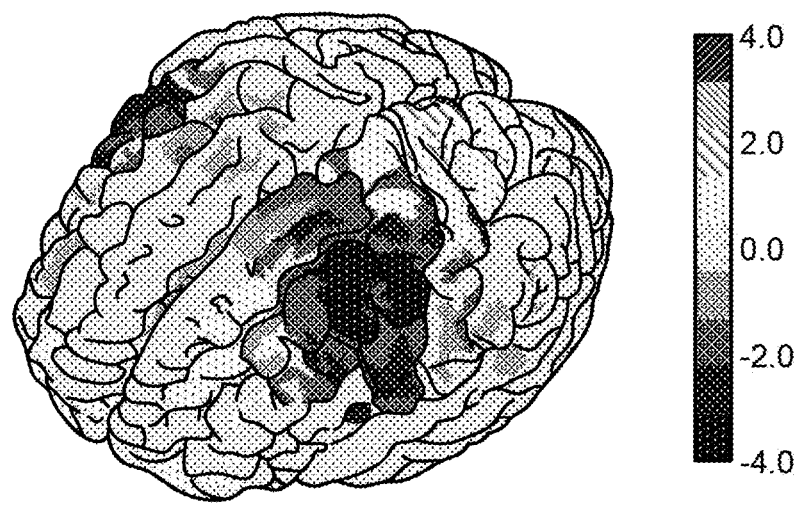
FIG. 12 is a diagram illustrating a first display example.

FIG. 12 is a diagram illustrating a first display example. The first display example illustrated in FIG. 12 is an example of the brain of a human in which spatial region values located 15 mm inward from the brain surface are observed on the brain surface. A polygon mesh is used for a curved surface indicating the brain surface. All vertices forming the polygon mesh are moved by 15 mm in an opposite direction of a pseudo-unit normal vector determined by an average method, and spatial region values at the moved positions are represented by colors at the vertices and displayed as a heat map.

Figure 13:
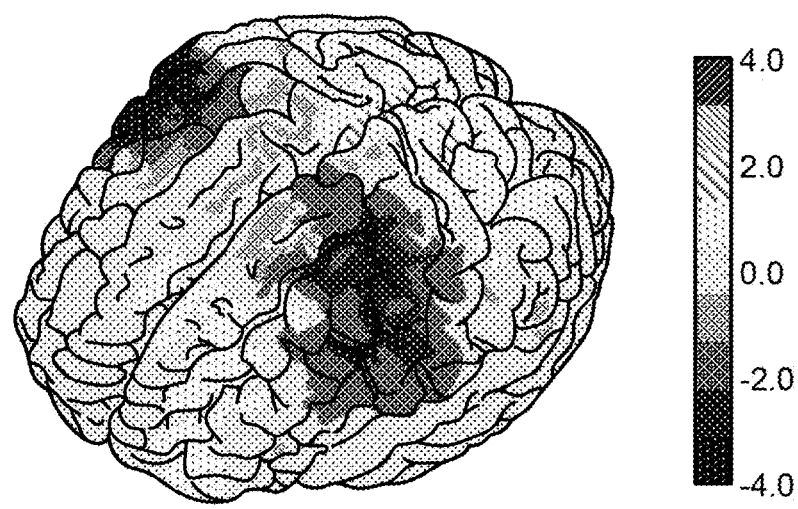
FIG. 13 is a diagram illustrating a second display example.

FIG. 13 is a diagram illustrating a second display example. The second display example illustrated in FIG. 13 is an example in which the movement distance is changed to 0 mm from the first display example illustrated in FIG. 12, that is, an example in which spatial region values on the brain surface are displayed. Comparing the first display example illustrated in FIG. 12 and the second display example illustrated in FIG. 13, it is understood that the spatial region values inside the brain are different from the spatial region values on the brain surface.

By using a bar for numerical input to successively change the movement distance, it is possible to change from the display example illustrated in FIG. 12 to the display example illustrated in FIG. 13, and change from the display example illustrated in FIG. 13 to the display example illustrated in FIG. 12.

In this manner, according to the first embodiment, spatial region values at positions obtained by offsetting sample points on the brain surface inward by a designated distance are represented by colors and projected on the brain surface, and interpolation processing is performed for the colors between sample points, so that the change in value can be represented in an easy-to-understand manner like a heat map. Consequently, the need for analogizing the position on the brain surface and the value by looking at several numbers of sectional diagrams like the conventional practice is eliminated, and the values inside the brain can be intuitively and easily observed on the brain surface.

In other words, according to the first embodiment, spatial region values located inside an organ can be observed on the organ surface, and what activity has occurred in the organ can be intuitively and easily grasped in association with the regions sectioned on the organ surface.

It is noted that, in the first embodiment, spatial region values indicating activity conditions in the brain measured by the brain magnetic field measurement device 3 are projected on a curved surface indicating the brain surface, but it is not limited thereto. For example, spatial region values indicating liver function conditions imaged by a positron emission tomography (PET) device instead of the brain magnetic field measurement device 3 may be projected on a curved surface indicating the surface of the liver as an organ.

Figure 14:
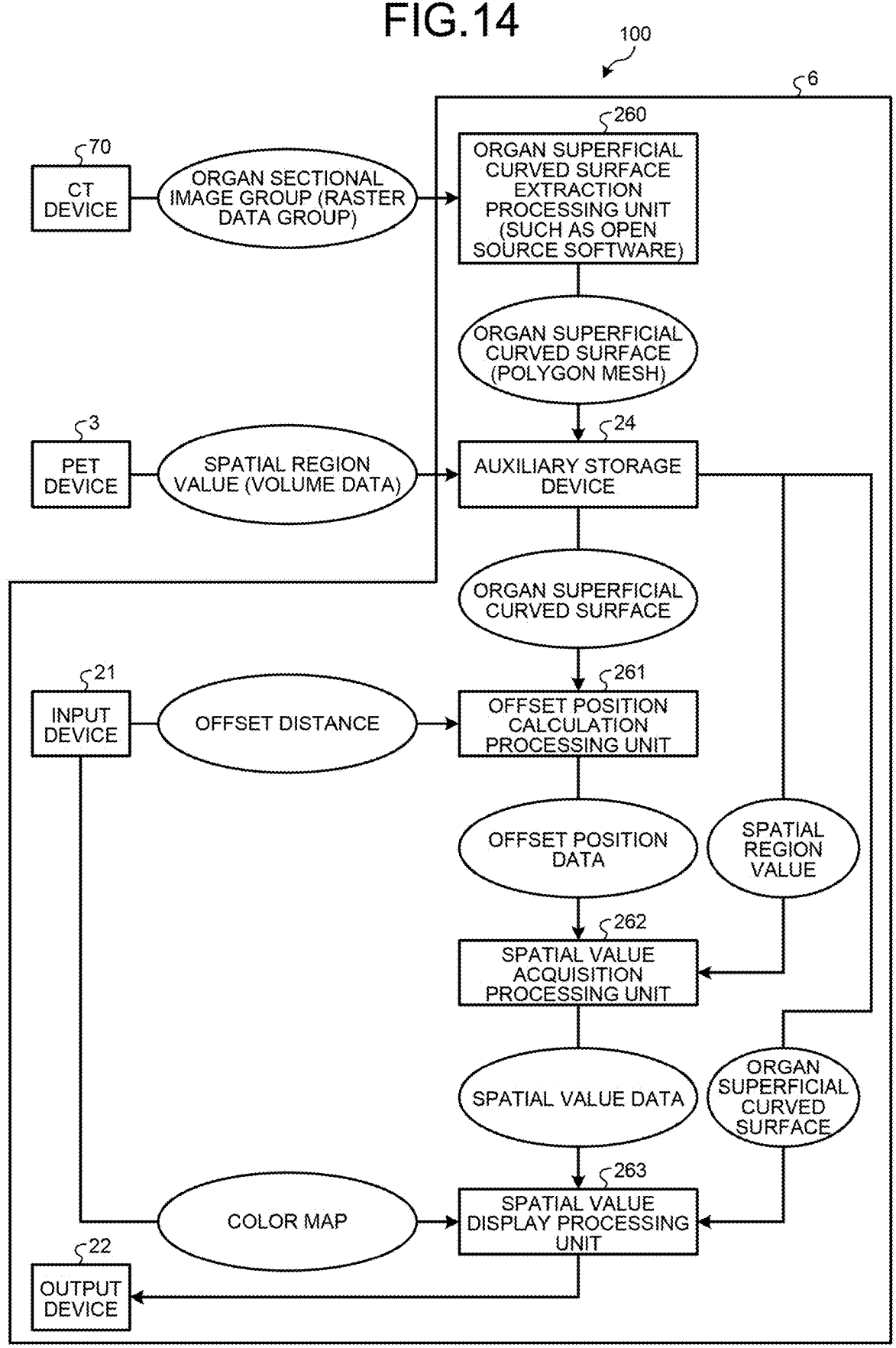
FIG. 14 is a block diagram illustrating a modification of the functions of the information processing device.

FIG. 14 is a block diagram illustrating a modification of the functions of the information processing device 6. An offset position calculation processing unit 261, a spatial value acquisition processing unit 262, and a spatial value display processing unit 263 illustrated in FIG. 14 are not different from the processing units described above with reference to FIG. 3.

In this manner, spatial region values at positions obtained by offsetting sample points on the liver surface inward by a designated distance are represented by colors and projected on the liver surface, and interpolation processing is performed for the colors between sample points, so that a change in value can be represented in an easy-to-understand manner like a heat map. The need for analogizing the position on the liver surface and the value by looking at several numbers of sectional diagrams like the conventional practice is eliminated, and the values inside the liver can be intuitively and easily observed on the liver surface.

Second Embodiment

Next, a second embodiment is described.

A biological information measurement system 100 in the second embodiment is different from the first embodiment in that spatial region values indicating internal conditions of an industrial product measured by non-destructive testing are projected on the product surface. In the following description of the second embodiment, descriptions of the same parts as in the first embodiment are omitted, and differences from the first embodiment are described.

Figure 15:
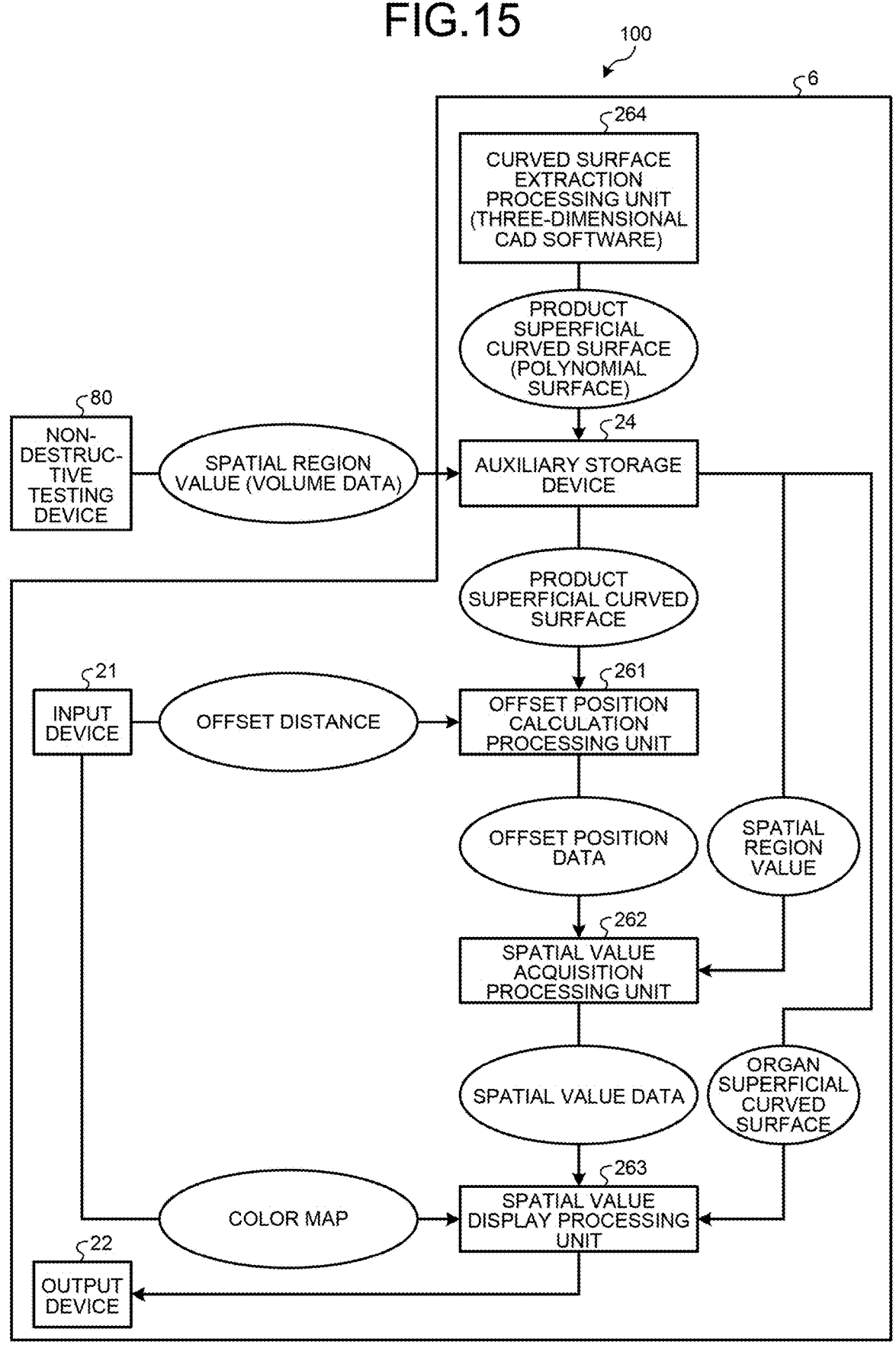
FIG. 15 is a block diagram for describing functions of an information processing device according to a second embodiment.

FIG. 15 is a block diagram for describing functions of an information processing device 6 according to the second embodiment. As illustrated in FIG. 15, the information processing device 6 is connected to a non-destructive testing device 80 instead of the brain magnetic field measurement device 3. The non-destructive testing device 80 detects harmful flaws (such as dents, cracks, and voids) without destructing a mechanical part or a structure (such as bridge, road, and ancient site) as a measurement target. The non-destructive testing device 80 detects an internal flaw by causing radiation or ultrasonic waves to enter a testing target, and detects a surface flaw by causing current or magnetic flux to flow near the surface.

The non-destructive testing device 80 outputs volume data (spatial region values) obtained by laminating sectional images of a mechanical part or a structure to be tested at a given interval, to the information processing device 6. The information processing device 6 stores the volume data (spatial region values) from the non-destructive testing device 80 in the auxiliary storage device 24.

As illustrated in FIG. 15, the information processing device 6 has a curved surface extraction processing unit 264. The arithmetic processing device 26 reads and executes three-dimensional CAD software stored in the auxiliary storage device 24 or the memory device 25 to implement the curved surface extraction processing unit 264.

The information processing device 6 has an offset position calculation processing unit 261, a spatial value acquisition processing unit 262, and a spatial value display processing unit 263.

The arithmetic processing device 26 reads and executes a biological information measurement program stored in the auxiliary storage device 24 or the memory device 25 to implement the offset position calculation processing unit 261, the spatial value acquisition processing unit 262, and the spatial value display processing unit 263. The processing units 261 to 263 are described in detail below.

First, the offset position calculation processing unit 261 is described.

The offset position calculation processing unit 261 first receives a product superficial curved surface represented by a polynomial surface group stored in advance from the auxiliary storage device 24, and receives an offset distance designated by a user from the input device 21. In the polynomial surface group, an ID is allocated for each polynomial surface (surface ID), and each polynomial surface is defined by a two-dimensional parameter space (u,v). It is noted that the offset distance may be stored in the auxiliary storage device 24 in advance and acquired from the auxiliary storage device 24 without using the input device 21.

The offset position calculation processing unit 261 next generates a sample point on each polynomial surface, and determines a position obtained by moving each sample point in an opposite direction of a unit normal vector of the polynomial surface by the designated offset distance. At this time, the offset position calculation processing unit 261 generates one or more sample points for an optional parameter (u,v). The offset position calculation processing unit 261 transfers the determined offset position to the spatial value acquisition processing unit 262 as offset position data.

FIG. 16 is a diagram exemplarily illustrating offset position data. As illustrated in FIG. 16, the offset position data is a list including sets each including a surface ID, parameters (u,v), and offset positional coordinates (X,Y,Z).

Next, the spatial value acquisition processing unit 262 is described.

The spatial value acquisition processing unit 262 first receives spatial region values represented by volume data stored in advance from the auxiliary storage device 24, and receives offset position data from the offset position calculation processing unit 261. Real scalar values as values of grid points are stored as the spatial region values, and the spatial region values are volume data formed in a rectangular parallelepiped space containing the product shape.

The spatial value acquisition processing unit 262 next acquires values for all positions stored in the offset position data from the spatial region values. At this time, the spatial value acquisition processing unit 262 acquires the values by using nearest neighbor interpolation.

The spatial value acquisition processing unit 262 transfers all the determined values (spatial region values at offset positions) to the spatial value display processing unit 263 as spatial value data.

FIG. 17 is a diagram exemplarily illustrating spatial value data. As illustrated in FIG. 17, the spatial value data is a list including sets each including a surface ID, parameters (u, v), and a scalar value meaning a value obtained from spatial region values.

Next, the spatial value display processing unit 263 is described.

The spatial value display processing unit 263 first receives a product superficial curved surface represented by a polynomial surface group stored in advance from the auxiliary storage device 24, receives spatial value data from the spatial value acquisition processing unit 262, and receives a color map designated by a user from the input device 21.

The color map is a list including sets each including a value and RGB color elements and arranged according to the value (see FIG. 11). The value means a value acquired from spatial region values. The RGB color elements mean a color corresponding to the value.

It is noted that a color of a value absent in the list is calculated by linear interpolation with colors of values before and after the value in the list. A color of a value smaller than the minimum value of the values in the list is set to the color of the minimum value in the list, and a color of a value larger than the maximum value of the values in the list is set to the color of the maximum value in the list.

Next, the spatial value display processing unit 263 determines colors corresponding to values stored in the spatial value data from the color map, and disposes a marker at the position of the parameter (u,v) on a corresponding polynomial surface and sets the color.

The spatial value display processing unit 263 generates an image in which the polynomial surface group and the marker are rendered, and transfers the image to the output device 22.

In this manner, according to the second embodiment, spatial region values, which are values at positions obtained by offsetting sample points on the surface of an industrial product inward by a designated distance and indicate internal conditions of the industrial product measured by non-destructive testing, are represented by colors and projected on the surface of the industrial product. Consequently, what test result is obtained at which depth from which position on the surface (internal conditions with respect to any surface site) can be intuitively and easily grasped. For example, repair work such as forming a hole by a drill and injecting a strengthening agent can be accurately performed.

Third Embodiment

Next, a third embodiment is described.

A biological information measurement system 100 in the third embodiment is different from the first embodiment in that spatial region values at positions obtained by offsetting positions of voxels on the surface of the organ shape to the inside of the organ shape are displayed at positions of the original voxels on the surface of the organ shape. In the following description of the third embodiment, descriptions of the same parts as in the first embodiment are omitted, and differences from the first embodiment are described.

Figure 18:
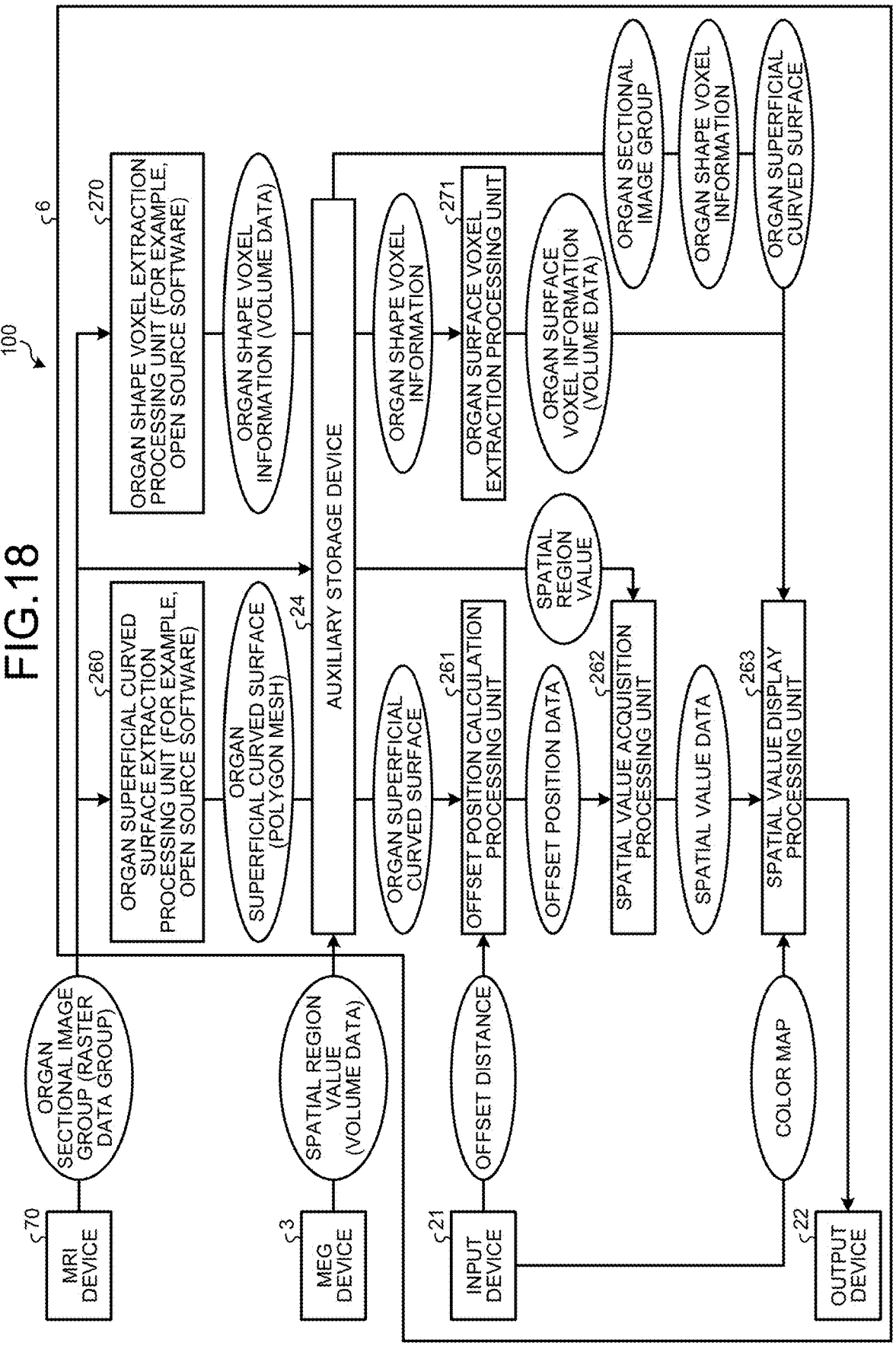
FIG. 18 is a block diagram for describing functions of an information processing device according to a third embodiment.

FIG. 18 is a block diagram for describing functions of an information processing device 6 according to the third embodiment. As illustrated in FIG. 18, the information processing device 6 according to the third embodiment has, in addition to the functional units illustrated in FIG. 3, an organ shape voxel extraction processing unit 270 and an organ surface voxel extraction processing unit 271. It is noted that, in the third embodiment, the information processing device 6 stores an organ section image group including an organ shape obtained from the biological structure acquisition device 70 such as an MR image device and an X-ray CT image device in the auxiliary storage device 24.

The organ shape voxel extraction processing unit 270 extracts organ shape voxel information (volume data), which is information on voxels at portions corresponding to an organ shape (brain shape) from an organ section image group including the organ shape obtained from the biological structure acquisition device 70 such as an MR image device and an X-ray CT image device, and stores the organ shape voxel information in the auxiliary storage device 24.

Figure 19:
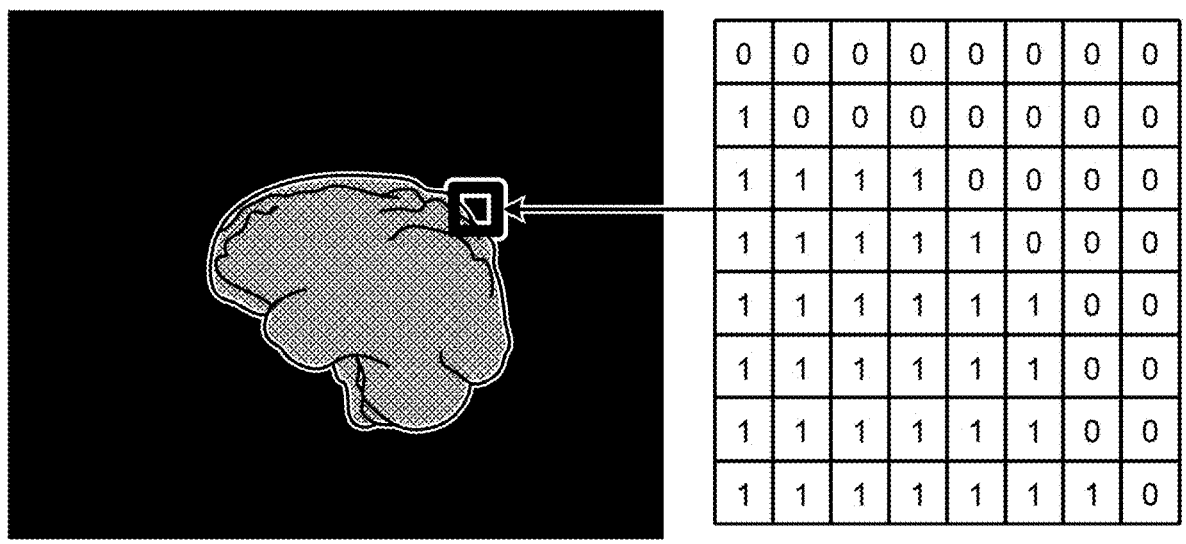
FIG. 19 is a diagram illustrating an example of organ shape voxel information (volume data).

FIG. 19 is a diagram illustrating an example of organ shape voxel information. The arithmetic processing device 26 reads and executes an organ shape voxel extraction program stored in the auxiliary storage device 24 or the memory device 25 to implement the organ shape voxel extraction processing unit 270. As the organ shape voxel extraction program, for example, well-known open source software (OSS) can be used.

Information on voxels in a portion corresponding to the organ shape is obtained by, as illustrated in FIG. 19, processing the volume data including the organ shape obtained by the biological structure acquisition device 70 such as an MR image device and an X-ray CT image device, setting the luminance values of the voxels in the portion corresponding to the organ shape to 1, and setting the luminance values of other voxels to 0.

The arithmetic processing device 26 reads and executes a biological information measurement program stored in the auxiliary storage device 24 or the memory device 25 to implement the organ surface voxel extraction processing unit 271.

The organ surface voxel extraction processing unit 271 first receives organ shape voxel information (volume data) from the auxiliary storage device 24, and investigates, for each voxel indicating the organ shape (brain shape), that is, each voxel with a luminance value of 1, whether all voxels adjacent in the up-down, left-right, and front-back directions are the organ shape (brain shape). In this case, when the all are the organ shape (brain shape), the organ surface voxel extraction processing unit 271 regards the voxel as the inside of the organ shape (brain shape), and when at least one is not the organ shape (brain shape), the organ surface voxel extraction processing unit 271 regards the voxel as the surface of the organ shape (brain shape). The organ surface voxel extraction processing unit 271 finally changes the luminance value of the voxel regarded as the inside of the organ shape (brain shape) to 0, and outputs the changed volume data to the spatial value display processing unit 263 as organ surface voxel information (volume data).

The voxel on the surface of the organ shape is a voxel around which there is at least one voxel not corresponding to the organ shape in a direction of the up-down, left-right, and front-back directions among voxels in a portion corresponding to the organ shape. It is noted that, when a voxel, all voxels around which in the up-down, left-right, and front-back directions correspond to the organ shape, the voxel is a voxel inside the organ shape.

To the spatial value display processing unit 263 in the third embodiment, the organ surface voxel information (volume data) from the organ surface voxel extraction processing unit 271 in addition to spatial value data (spatial region values) processed by the spatial value acquisition processing unit 262 are input, and an organ section image group, organ shape voxel information, and an organ superficial curved surface from the auxiliary storage device 24 are input. The spatial value display processing unit 263 in the third embodiment represents a display material corresponding to acquired spatial value data (spatial region values) by a color, and when volume data is used for surface shape data, allocates a color to a voxel in the volume data as an attribute and performs interpolation processing for colors at positions other than a position of the voxel to generate a color volume rendering image. The details are described below.

The spatial value display processing unit 263 first receives an organ section image group, organ shape voxel information, and an organ superficial curved surface stored in advance from the auxiliary storage device 24, receives spatial value data (spatial region values) from the spatial value acquisition processing unit 262, receives organ surface voxel information from the organ surface voxel extraction processing unit 271, and receives a color map designated by a user from the input device 21. It is noted that the color map and the usage thereof are the same as in the first embodiment.

Figure 20A:
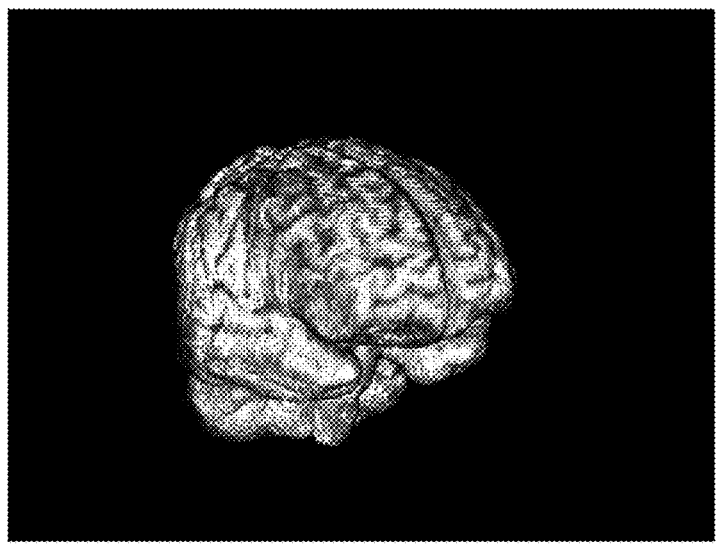
FIGS. 20A and 20B are diagrams illustrating an organ section image group.
Figure 20B:
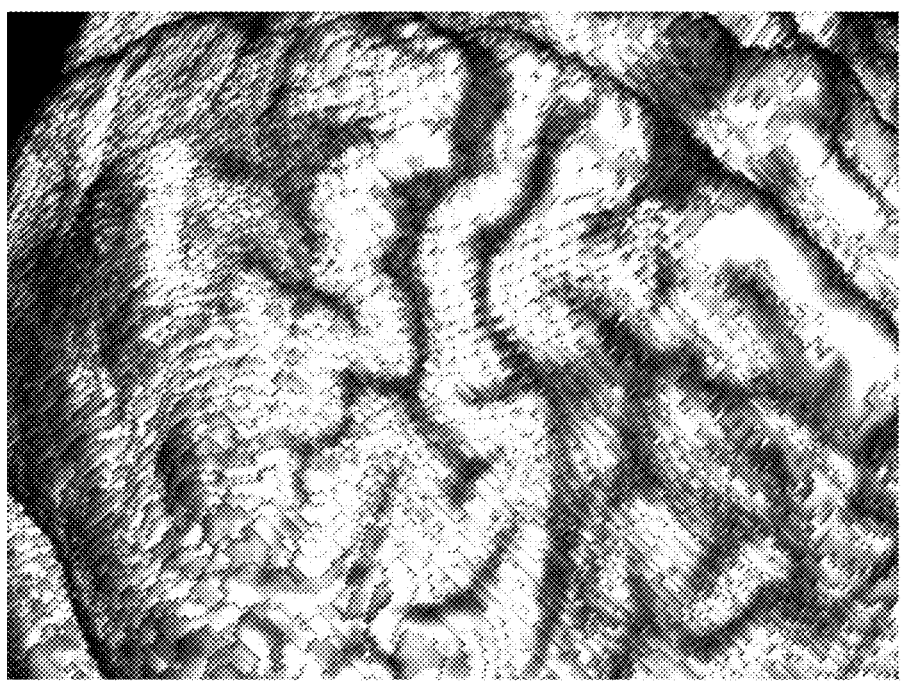

Next, the spatial value display processing unit 263 sets, for volume data on the organ section image group, luminance values of voxels corresponding to voxels other than the organ shape (brain shape) obtained from the organ shape voxel information to 0. FIGS. 20A and 20B are diagrams illustrating an organ section image group. FIG. 20A is a diagram illustrating the entire image, and FIG. 20B is an enlarged diagram in which a part is enlarged. As illustrated in FIGS. 20A and 20B, volume data on the organ section image group is volume data in which only the organ shape (brain shape) is displayed.

Next, the spatial value display processing unit 263 determines, for each voxel on the surface of the organ shape obtained from the organ surface voxel information, vertices of a polygon mesh located at the closest position from the organ superficial curved surface. The spatial value display processing unit 263 determines colors corresponding to values stored in the spatial value data from the color map, and sets the colors to the vertices of voxels on the surface of the organ shape.

Next, spatial value display processing unit 263 provides, for volume data on the organ section image group, the color determined for each voxel on the surface of the organ shape to a voxel in the organ section image group corresponding to each voxel on the surface of the organ shape as an attribute.

Finally, the spatial value display processing unit 263 generates a color volume rendering image for volume data on the organ section image group, and transfers the color volume rendering image to the output device 22. In this case, colors other than those at the positions of voxels are subjected to interpolation processing based on an interpolation method and rendered. It is noted that examples of the interpolation method include linear interpolation (tri-linear interpolations).

Figure 21A:
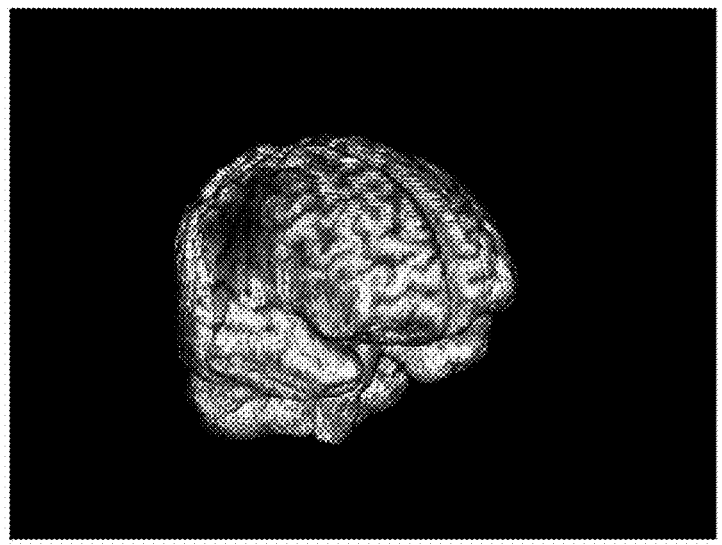
FIGS. 21A and 21B are diagrams illustrating a display example of a color volume rendering image.
Figure 21B:
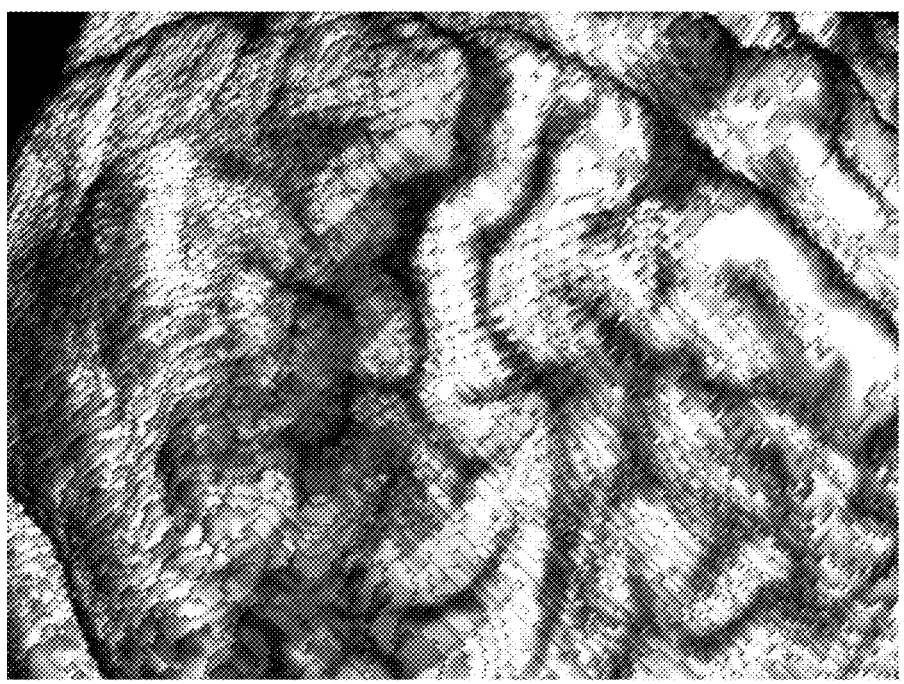

FIGS. 21A and 21B are diagrams illustrating a display example of a color volume rendering image. FIG. 21A is a diagram illustrating the entire image, and FIG. 21B is an enlarged diagram in which a part is enlarged. In the cases of the surfaces illustrated in FIG. 12 and FIG. 13, shades are provided depending on angles with respect to a rendering light source, but the densities of colors of individual triangles forming polygon meshes are uniform. On the other hand, in the case of the color volume rendering image, as illustrated in FIGS. 21A and 21B, shades are provided depending on an angle with respect to the light source, and the densities are provided to voxels forming volumes as individual luminances. Thus, in the case of the color volume rendering image illustrated in FIGS. 21A and 21B, when the organ surface is overlooked, what is called unevenness in portions with high luminance and portions with low luminance can be observed. Comparing a sulcus pattern in the enlarged diagram in FIGS. 20A and 20B and a sulcus pattern in the enlarged diagram in FIGS. 21A and 21B, it is understood that unevenness in portions with high luminance and portions with low luminance is displayed in the color volume rendering image illustrated in FIGS. 21A and 21B. The unevenness is caused due to the difference in conditions such as compositions of sites of the organ when photographing the organ by the biological structure acquisition device 70 such as an MR image device and an X-ray CT image device. In other words, the color volume rendering image is a rendering image more realistic than the original image taken by the biological structure acquisition device 70 such as an MR image device and an X-ray CT image device.

According to the third embodiment as described above, the values in a spatial region inside the organ can be observed on volume data on an original image obtained by the biological structure acquisition device 70 such as an MR image device and an X-ray CT image device, and hence the values in the spatial region can be evaluated by collating with a larger amount of information such as the texture of the organ surface.

It is noted that, as a method for displaying a spatial region value at the position of a voxel, some methods are conceivable, such as a method for representing a display material corresponding to the spatial region value by a color as described above and a method for representing a display material corresponding to the spatial region value by a figure (for example, circle). Any method may be used as long as the difference in spatial region value can be recognized by the representation. For a position other than the position of a voxel, a value obtained by interpolating values displayed at surrounding voxel positions may be displayed to make it easier to grasp a change in value like a heat map.

It is noted that, in the third embodiment, spatial region values indicating activity conditions in the brain measured by the brain magnetic field measurement device 3 are projected at the positions of original voxels on the brain shape surface, but the embodiment is not limited thereto. For example, spatial region values indicating liver function conditions imaged by a positron emission tomography (PET) device instead of the brain magnetic field measurement device 3 may be projected at the positions of voxels on the shape surface of a liver as an organ.

In this manner, the values in a spatial region inside a liver can be observed on volume data on an original image obtained by the biological structure acquisition device 70 such as an MR image device and an X-ray CT image device, and hence the values in the spatial region can be evaluated by collating with a larger amount of information such as the texture of the liver surface.

An embodiment provides an advantageous effect that spatial region values located inside a measurement target can be observed on the surface of the measurement target, and hence what activity has occurred in the measurement target can be intuitively and easily grasped in association with regions sectioned on the surface of the measurement target.

The above-described embodiments are illustrative and do not limit the present invention. Thus, numerous additional modifications and variations are possible in light of the above teachings. For example, at least one element of different illustrative and exemplary embodiments herein may be combined with each other or substituted for each other within the scope of this disclosure and appended claims. Further, features of components of the embodiments, such as the number, the position, and the shape are not limited the embodiments and thus may be preferably set. It is therefore to be understood that within the scope of the appended claims, the disclosure of the present invention may be practiced otherwise than as specifically described herein.

The method steps, processes, or operations described herein are not to be construed as necessarily requiring their performance in the particular order discussed or illustrated, unless specifically identified as an order of performance or clearly identified through the context. It is also to be understood that additional or alternative steps may be employed.

Further, any of the above-described apparatus, devices or units can be implemented as a hardware apparatus, such as a special-purpose circuit or device, or as a hardware/software combination, such as a processor executing a software program.

Further, as described above, any one of the above-described and other methods of the present invention may be embodied in the form of a computer program stored in any kind of storage medium. Examples of storage mediums include, but are not limited to, flexible disk, hard disk, optical discs, magneto-optical discs, magnetic tapes, non-volatile memory, semiconductor memory, read-only-memory (ROM), etc.

Alternatively, any one of the above-described and other methods of the present invention may be implemented by an application specific integrated circuit (ASIC), a digital signal processor (DSP) or a field programmable gate array (FPGA), prepared by interconnecting an appropriate network of conventional component circuits or by a combination thereof with one or more conventional general purpose microprocessors or signal processors programmed accordingly.

Each of the functions of the described embodiments may be implemented by one or more processing circuits or circuitry. Processing circuitry includes a programmed processor, as a processor includes circuitry. A processing circuit also includes devices such as an application specific integrated circuit (ASIC), digital signal processor (DSP), field programmable gate array (FPGA) and conventional circuit components arranged to perform the recited functions.

What is claimed is:

1. An information processing device comprising:
   a memory storing computer readable instructions; and
   processing circuitry configured to execute the computer readable instructions to,
   determine displaced position data on a position displaced from a curved surface point on three-dimensional (3D) surface shape data on a surface of a measurement target in a given direction by a given distance,
   determine volume data of the measurement target, the volume data formed in a 3D space containing a 3D shape of the measurement target and the displaced position data,
   determine a spatial region value for a position stored in the displaced position data based on the volume data of the measurement target and the displaced position data, and
   display a display material corresponding to the spatial region value on the 3D surface shape data.

2. The information processing device according to claim 1, wherein the given direction from the curved surface point is an opposite direction of a unit normal vector.

3. The information processing device according to claim 2, wherein the processing circuitry is further configured to:
   in a case where the measurement target is a brain and the position enters a self-interference region, determine, as an offset position, a position immediately before entering the self-interference region.

4. The information processing device according to claim 1, wherein the processing circuitry is further configured to determine a unit normal vector using an average method.

5. The information processing device according to claim 1, wherein the processing circuitry is further configured to represent a display material corresponding to an acquire spatial region value by a color, and in a case where a polygon mesh is used for the surface shape data, allocates a color to each vertex of the polygon mesh and allocates a color in a polygon region other than vertices by interpolation processing.

6. The information processing device according to claim 5, wherein the processing circuitry is further configured to use Gouraud shading for the interpolation processing.

7. The information processing device according to claim 1, wherein the processing circuitry is further configured to:
   represent a display material corresponding to an acquired spatial region value by a color, and when volume data is used for the surface shape data, allocate a color as an attribute to a voxel in the volume data and perform interpolation processing for colors at positions other than a position of the voxel to generate a color volume rendering image.

8. The information processing device according to claim 7, wherein the processing circuitry is further configured to use linear interpolation for the interpolation processing.

9. The information processing device according to claim 1, wherein the processing circuitry is further configured to:
   form 3D grid points at desired intervals of the 3D space containing the 3D shape of the measurement target;
   set real scalar values corresponding to coordinate positions of the 3D grid points; and
   determine the spatial region values based on the set real scalar values of the 3D grid points and the displaced position data.

10. The information processing device according to claim 1, wherein the processing circuitry is further configured to:
    calculate a polygon mesh to represent the 3D surface shape data.

11. The information processing device according to claim 10, wherein the processing circuitry is further configured to:
    generate spatial value data based on the polygon mesh, the spatial value date including a list of vertex IDs and scalar values, the vertex IDs associated with vertexes of the polygon mesh, and the scalar values corresponding to the spatial region value at the respective vertex.

12. A biological information measurement device, comprising:
    a memory having computer readable instructions stored thereon; and
    processing circuitry configured to execute the computer readable instructions to,
    determine displaced position data on a position displaced from a curved surface point on three-dimensional (3D) surface shape data on an organ surface in a given direction by a given distance,
    determine volume data of the measurement target, the volume data formed in a 3D space containing a 3D organ shape, and the displaced position data,
    determine a spatial region value for a position stored in the displaced position data based on the volume data of the measurement target and the displaced position data, and
    display a display material corresponding to the spatial region value on the 3D surface shape data.

13. The biological information measurement device according to claim 12, wherein the given direction from the curved surface point is an opposite direction of a unit normal vector.

14. The biological information measurement device according to claim 13, wherein the processing circuitry is further configured to:
    in a case where the measurement target is a brain and the position enters a self-interference region, determine, as an offset position, a position immediately before entering the self-interference region.

15. The biological information measurement device according to claim 12, wherein the processing circuitry is further configured to determine a unit normal vector using an average method.

16. The biological information measurement device according to claim 12, wherein the processing circuitry is further configured to represent a display material corresponding to an acquire spatial region value by a color, and in a case where a polygon mesh is used for the surface shape data, allocates a color to each vertex of the polygon mesh and allocates a color in a polygon region other than vertices by interpolation processing.

17. The biological information measurement device according to claim 16, wherein the processing circuitry is further configured to use Gouraud shading for the interpolation processing.

18. A non-transitory computer-readable medium including programmed instructions, which when executed by a computer, cause the computer to:

determine displaced position data on a position displaced from a curved surface point on three-dimensional (3D) surface shape data on a surface of a measurement target in a given direction by a given distance;

determine volume data of the measurement target, the volume data formed in a 3D space containing a 3D shape of the measurement target and the displaced position data;

determine a spatial region value for a position stored in the displaced position data based on the volume data of the measurement target and the displaced position data; and display a display material corresponding to the spatial region value on the 3D surface shape data.

19. The non-transitory computer-readable medium according to claim 18, wherein the given direction from the curved surface point is an opposite direction of a unit normal vector.

20. The non-transitory computer-readable medium according to claim 19, wherein the computer is further caused to:

in a case where the measurement target is a brain and the position enters a self-interference region, determine, as an offset position, a position immediately before entering the self-interference region.

* * * * *